United States Patent [19]

Maguire

[11] Patent Number: 5,262,644
[45] Date of Patent: Nov. 16, 1993

[54] REMOTE SPECTROSCOPY FOR RAMAN AND BRILLOUIN SCATTERING

[75] Inventor: John F. Maguire, San Antonio, Tex.

[73] Assignee: Southwest Research Institute, San Antonio, Tex.

[21] Appl. No.: 993,446

[22] Filed: Dec. 16, 1992

Related U.S. Application Data

[63] Continuation of Ser. No. 875,521, Apr. 27, 1992, abandoned, which is a continuation of Ser. No. 732,996, Jul. 18, 1991, abandoned, which is a continuation of Ser. No. 546,419, Jun. 29, 1990, abandoned.

[51] Int. Cl.$^5$ .................................................. G01N 21/65
[52] U.S. Cl. ........................................ 250/339; 356/73; 356/301; 356/346
[58] Field of Search ............... 356/301, 73, 43, 44, 356/337, 338, 339, 346; 250/338.1, 339

[56] References Cited

U.S. PATENT DOCUMENTS

| | | | |
|---|---|---|---|
| 3,906,241 | 9/1975 | Thompson | 250/574 |
| 4,184,171 | 1/1980 | Panish | 372/45 |
| 4,411,525 | 10/1983 | Ogawa | 356/339 |
| 4,472,052 | 9/1984 | Löfgren | 356/43 |
| 4,509,212 | 4/1985 | Baker | 356/409 |
| 4,573,761 | 3/1986 | McLachlan et al. | 356/301 |
| 4,620,284 | 10/1986 | Schnell et al. | 356/301 |
| 4,678,277 | 7/1987 | Delhaye et al. | 356/301 |
| 4,767,219 | 8/1988 | Bibby | 356/301 |
| 4,781,458 | 11/1988 | Angel et al. | 356/301 |
| 4,802,761 | 2/1989 | Bowen et al. | 356/301 |
| 4,856,897 | 8/1989 | Fateley et al. | 356/333 |
| 4,867,564 | 9/1989 | Sweeney et al. | 356/43 |

FOREIGN PATENT DOCUMENTS

| | | | |
|---|---|---|---|
| 2571144 | 4/1986 | France | 356/301 |
| 61-160046 | 9/1985 | Japan | 356/301 |
| 8706011 | 10/1987 | PCT Int'l Appl. | 356/301 |

OTHER PUBLICATIONS

Archibald et al., "Raman Spectroscopy over Optical Fibers with the Use of a Near-IR FT Spectrometer", Appl. Spectroscopy 42(8), 1988, pp. 1558-1563.

Bello et al., "Surface-Enhanced Raman Scattering Fiber-Optic Sensor", Applied Spectroscopy, 44 (1), Jan. 1990, pp. 63-69.

E. Neil Lewis, et al., "Extending the Vibrational Limits in Near-Infrared Fourier Transform Raman Spectroscopy", *Applied Spectroscopy*, 1989, vol. 43, No. 1, pp. 156-159.

H. Stammreich, "High-Resolution Raman Spectroscopy in the Red and Near Infra-red", *Spectrochlmica Acta*, 1961, vol. 17, pp. 775-784.

D. J. Gardiner & P. R. Graves, *Practical Raman Spectroscopy*, 1989, Springer-Verlag.

*Primary Examiner*—Carolyn E. Fields
*Attorney, Agent, or Firm*—Baker & Botts

[57] ABSTRACT

An apparatus and method for performing Raman and Brillouin spectroscopy remotely. A near-infrared laser is used to irradiate a sample of material to be analyzed. Optical fibers transmit incident radiation from a near-infrared radiation source to the sample, and transmit Raman and Brillouin scattered radiation from the sample to the detecting equipment. The incident radiation is carefully determined so as to avoid fluorescence and to limit optic fiber losses. The invention provides useful information with the use of an interferometer.

16 Claims, 4 Drawing Sheets

REMOTE SPECTROSCOPY FOR RAMAN AND BRILLOUIN SCATTERING

This application is a continuation of application Ser. No. 07/875,521, filed Apr. 27, 1992, entitled "Remote Raman Spectroscopy" by John F. Maguire, now abandoned; which is a continuation of application Ser. No. 07/732,996, filed Jul. 18, 1991, by John F. Maguire, now abandoned; which is a continuation of application Ser. No. 07/546,419, filed Jun. 29, 1990, by John F. Maguire, all now abandoned.

TECHNICAL FIELD OF THE INVENTION

This invention relates to spectroscopy, and more particularly to Raman and Brillouin spectroscopy using near a infrared light source and optical fibers for sensing and receiving so that materials analysis can be performed remotely.

BACKGROUND OF THE INVENTION

Raman spectroscopy is the name given to a technique whereby monochromatic electromagnetic radiation is used to irradiate a sample of material and the spectral distribution of the scattered radiation is analyzed. The incident radiation, which is traditionally in the visible region of the spectrum, excites the molecules of the material and causes them to undergo spontaneous emission of radiation. The frequency of the light that is scattered in this manner is modulated by the natural frequencies associated with the intramolecular and the intermolecular interactions of the molecules. The result is a series of spectral lines that are much weaker and shifted in frequency relative to the incident wavelength.

Because the intensity of the scattered radiation is weak compared to that of the incident radiation, the incident radiation must be of a relatively high intensity if the spectrum is to be observable. To provide a high intensity incident radiation, lasers typically are used as the light source for Raman spectroscopy.

A problem with Raman spectroscopy is the tendency of many sample materials to fluoresce when subjected to the incident radiation. This fluorescence dominates the signal and obscures the underlying Raman signal, which contains much of the useful information. As a result, until recently, Raman spectroscopy was mostly used in laboratory experiments with optically non-fluorescent compounds or with compounds with limited fluorescence.

If a near-infrared radiation source is used, as opposed to a visible light source, there is less fluorescence. However, disadvantages of near infrared spectroscopy are that the resulting signal is weak and infrared detectors are much less sensitive than those used for visible light.

The most recent applications of Raman spectroscopy for industrial samples use near-infrared excitation with laser radiation sources, infrared-sensitive detectors, and sophisticated Fourier transform data analysis. However, this methodology requires the availability of a sample of the material to be tested at the site of the test equipment. A sample must be collected off-line and transported and stored in a container suitable for the scattering process.

Attempts to achieve remote sample handling have accompanied advances in optic fiber technology. For example, absorption spectroscopy methods, as opposed to scattering methods, have attempted to achieve remote analysis of materials, using fiber optic transmission. These absorption methods have been only somewhat successful. Mid-infrared absorption methods attempt to avoid the fluorescence problems associated with visible and ultraviolet absorption methods, but suffer from problems with the optic fibers, such as high attenuation, fragility, and toxicity. Near-infrared absorption is suited to remote fiber optic sampling, but the response signal only contains a number of high frequency overtone bands, which are not useful for analysis of the fundamental vibrational frequencies of many organic and polymeric materials.

Optical fiber methods using scattering methods, such Raman spectroscopy, have also met with limited success. One recent patent, U.S. Pat. No. 4,802,761, discloses a method and apparatus that uses an optical fiber to transmit radiation from a laser to a sample-containing cell. Backscattered Raman radiation is then transmitted via collecting optical fibers to a detection system. The laser is a pulsed laser, tunable from 220 to 900 nanometers. The patent disclosure recognizes the problems associated with fluorescence, and the invention attempts to overcome these problems by tuning the laser to a different wavelength. Although the patent disclosure acknowledges that using longer incident wavelengths would alleviate fluorescence, it states that infrared spectroscopy is not amenable to fiber optic transmissions. Another patent, U.S. Pat. No. 3,906,241, also uses optical fibers for transmitting visible laser-generated light and collecting Raman radiation. The patent disclosure does not address the problems associated with fluorescence.

A recently published reference, Practical Raman Spectroscopy, edited by D. J. Gardiner and P. R. Graves (1989), notes the advantages of combining near infrared Raman spectroscopy with optical fiber technology, together with Fourier transform methods of analysis. This publication discusses the difficulty of removing the exciting line wavelength from the scattered radiation and an attendant need for Fourier transform instrumentation that is expensive and delicate.

Thus, a need exists for improved spectroscopic techniques that permit fiber optic transmission. These techniques should permit instrumentation that is rugged and inexpensive and thus suited for commercial and industrial use.

SUMMARY OF THE INVENTION

An object of the invention is to provide spectroscopic information that is as useful as that provided by mid-infrared absorption methods, but which may be obtained remotely, using fiber optics. An underlying feature of the invention is that, unlike prior attempts in the background art to accomplish fiber optic spectroscopy, which focus on improving the frequency analysis end of the spectroscopic process, the focus is on the incident radiation, detector, and fiber optic coupling. Consistent with this approach, the invention involves identifying a specific range of incident radiation, that will work with a particular arrangement of instrumentation, a type of radiation response, and an analysis technique.

Accordingly, one aspect of the invention is an apparatus for remotely performing a spectroscopic analysis of Raman scattered radiation from a sample that is illuminated by a monochromatic near-infrared source. A near-infrared laser provides incident radiation, which has a wavelength within a range of wavelengths between a fluorescence limit and a fiber optics loss limit. Low loss fiber optics are used to transmit the incident radiation and to collect radiation that is scattered by the material in response to the incident radiation. A dispersive frequency analyzer, such as a monochrometer, captures a predetermined wavelength of the scattered radiation, and an infrared detector detects the radiation and produces an electronic signal representing its intensity. This signal is used to provide some form of output that can be used analytically to determine how the material compares to a reference.

A technical advantage of the invention is that, like all spectroscopic techniques, it provides a nondestructive technique for determining the identity and structure of organic compounds. Also, the invention permits this analysis to be performed remotely, without the need for physical proximity between the spectroscope and the material under test. Thus, the invention permits the remote analysis, with distances as large several kilometers between the sample and the instrumentation, of samples in hostile or physically inaccessible environments. Because the invention uses the frequency shifts associated with Raman scattering at near-infrared wavelengths, it may be used even with compounds that fluoresce. The analyzing instrumentation may be made simple and inexpensive, without the need for complicated data processing.

DETAILED DESCRIPTION OF THE INVENTION

Figure 1:
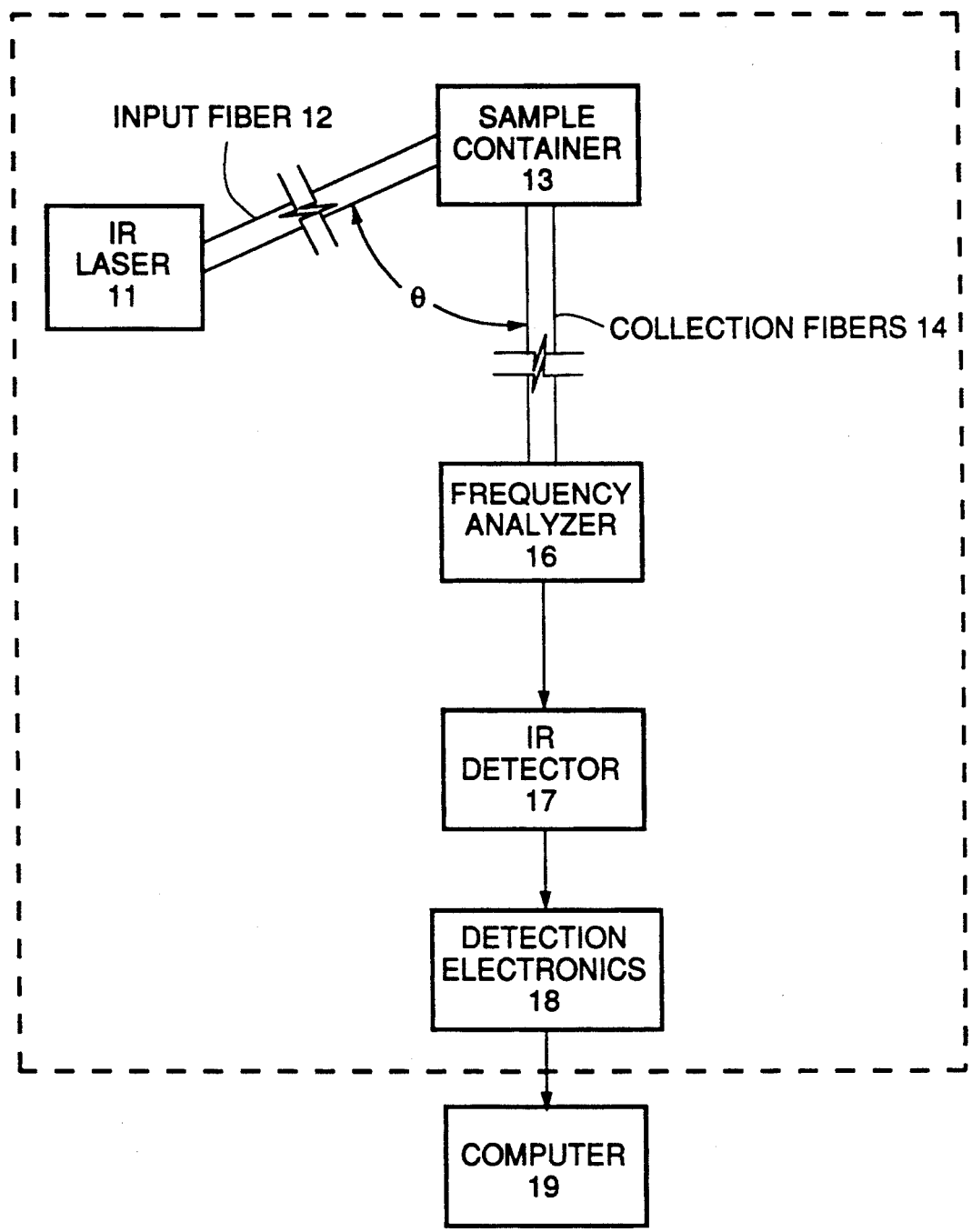
FIG. 1 is a block diagram of a Raman spectroscope having an infrared radiation source, an optic input fiber and optic collection fibers, and an infrared detector.

FIG. 1 is a block diagram of a near-infrared laser Raman spectroscope 10 having fiber optic input and collection fibers 12 and 14. A sample container 13 holds an amount of the sample under test. An advantage of the invention is that the material to be analyzed may be optically opaque or otherwise have characteristics that cause the material to fluoresce when exposed to visible light.

The amount of the sample is not important, and container 13 may be any size or shape. In fact, as explained below in connection with FIG. 4, in practical applications of the invention, spectroscope 10 may be used in-situ and in real-time. Thus, container 13 could be part of any system in which a material is to be analyzed. For example, the analysis could be of a chemical during a manufacturing process, and container 13 could be a processing vat. Also, the "sample" could be a component of a piece of equipment.

A infrared radiation source 11 emits radiation of a known wavelength or wavelengths, which is transmitted to container 13 via an optical input fiber 12. In the preferred embodiment, radiation source 11 is a coherent source, such as a laser, for providing radiation in the near infrared region of the electromagnetic spectrum. In fact, an important feature of the invention is the identification of a spectral window in which the apparatus of FIG. 1 is useful. Inelastic scattering in this region gives rise to modulated radiation, which falls within the transmission curves for certain fiber optics glasses. In particular, the window is in the 1.0 micrometer to 2.0 micrometer range, such that the fiber optic transmission losses are much less than 20 dB per kilometer, which is typical of chalcogenide fiber optic glasses used in prior remote spectroscopic methods. The upper limit, where the wavelength is so long that the result is unacceptable fiber optic losses is referred to herein as the "fiber optic loss limit". The lower limit, wherein the wavelength is so short so as to result in unacceptable fluorescence is referred to herein as the "fluorescence limit".

An example of a suitable radiation source 11 is a Nd:YAG (yttrium aluminum garnet) laser operating at 9398 $cm^{-1}$, where $cm^{-1}$ denotes a wavenumber in terms of reciprocal wavelength in centimeters. The 9398 $cm^{-1}$ wavenumber corresponds to a 1064 nm wavelength. A krypton ion laser may also be suitable. In the preferred embodiment, a continuous wave rather than a pulsed laser is used. The radiation emitted by radiation source 11 is referred to herein as the "incident radiation."

The radiation from radiation source is focused into one end of a length of a fiber optic input tube 12. The other end of input fiber 12 is unclad and embedded in, or otherwise in close proximity to the sample, so that the radiation will pass into the sample.

As the incident radiation passes through the sample, a part of the radiation is scattered. The sample material is therefore excited with the incident radiation, and produces radiation of different wavelengths from that of the incident radiation. This scattered radiation is referred to herein as the "Raman radiation".

As stated above, input fiber 12 is a fiber optics channel. A feature of the invention is the recognition that if radiation source were in the mid-infrared region, the incident radiation into transmission tube 14 would be close to the "phonon edge". The result is that the radiation is absorbed rather than transmitted through the fiber optic.

To overcome the losses associated with many fiber optics glasses, the selection of the glasses for input fiber 12 is important to the operation of the invention. An example of a suitable fiber for input fiber 12 is a fiber comprised of a heavy-metal fluoride, such as zirconium fluoride. Quartz fibers could also be used with satisfactory results. Optical fibers made from these glasses are referred to herein as "low loss fibers", in that they are characterized by high optical quality and low intrinsic scatter. Ideally, the losses from these low loss fibers are less than 0.01 dB $km^{-1}$. Losses of this order of magnitude permit remote sensing over distances of over 1000 meters.

In the process of the Raman scattering, the incident photons either gain or lose energy appropriate to molecular vibrational frequencies, i.e., in a range of 200 to 3500 $cm^{-1}$, with the gain being associated with anti-Stokes scattering and the loss being associated with Stokes scattering. The incident photons are thus frequency modulated and scattered.

Collection fibers 14 receive some of the secondarily scattered photons. This radiation may be frequency analyzed in the range of $9398^{-1}$ to $5898^{-1}$ (Stokes) or $9398^{-1}$ to 12898 $cm^{-1}$ (Anti-Stokes), both being within plus or minus 3500 $cm^{-1}$ from the incident frequency. These frequency shifts cover the region of spectral interest for most organic molecules and polymers. As stated above, analyzing the frequency shifts of Raman scattered radiation in the near infrared avoids the loss problems associated with mid infrared methods. The methods of analysis are discussed in further detail below in connection with FIGS. 2 and 3.

Frequency analyzer 18 may be either a monochrometer or interferometer. Monochrometers, which are associated with dispersed wavelengths and the measuring of intensity at a single wavelength, may be implemented with simple instrumentation. On the other hand, interferometers are associated with Fourier transform techniques, and are typically associated with relatively sophisticated instrumentation. An advantage of the invention is that it permits sufficient resolution in the spectral area of interest, such that Fourier transform techniques need not be used. This permits the use of simple and robust equipment having no moving parts and no need for sophisticated computational capability.

Thus, in one embodiment of the invention, a dispersive frequency analyzer 16, such as a monochrometer, is used to separate the Raman radiation into its constituent wavelengths. The monochrometer may be either a grating or filter monochrometer. Also, depending on the desired resolution, a single, double, or triple monochrometer may be used. As will be explained in further detail below, in a simple practical application, frequency analyzer 16 may be a monochrometer set so that a predetermined wavelength will be captured.

Alternatively, frequency analyzer 16 may be comprised of an interferometer. An example of a suitable interferometer is a Michelson interferometer, which scans the infrared spectrum. If an interferometer is used, a data processing device 19 is in communication with detector 17 for achieving the Fourier transform analysis.

Infrared detector 17 detects the photons at the various wavelength or wavelengths provided by frequency analyzer 16, and gives an output that is a measure of the intensity of the Raman radiation at each wavelength. If a monochrometer is used, detector 17 receives radiation at whatever frequency is selected by means of the grating or filter. If an interferometer is used, detector 17 receives a fringe pattern representing some integral function of frequency, of which the Fourier transform is a frequency spectrum.

Because detector 17 must be sensitive to infrared radiation, the choice of detector 17 is a significant feature of the invention. Thus, detector 17 may be a solid state detector, which offers a high sensitivity to infrared radiation. Examples of suitable devices for use as detector 17 are germanium and indium gallium arsenide cooled detectors. Depending on the application, a diode array may be used.

Detector electronics 18 includes amplification devices for providing a more easily interpreted signal. If a data processing device 19 is used, detector electronics 18 includes a digitization means.

Data processor 19 receives digitized signals representing the output of detector 19. It provides an analysis of the chemical signature of the sample. As explained below, data processor may be a fairly sophisticated device, such as a computer, or may be simply a means for providing an output so that the signal from detector electronics 18 may be compared to a reference.

The operation of the invention can vary in complexity according to the application and the needs of the user. For example, in relatively sophisticated applications, a spectrum of scattered radiation can be obtained and its specific features such as peak position, intensity, and profile, used to reveal information about the sample. On the other hand, a simple application might merely compare the intensity of the scattered radiation at a single wavelength to a reference.

Figure 2:
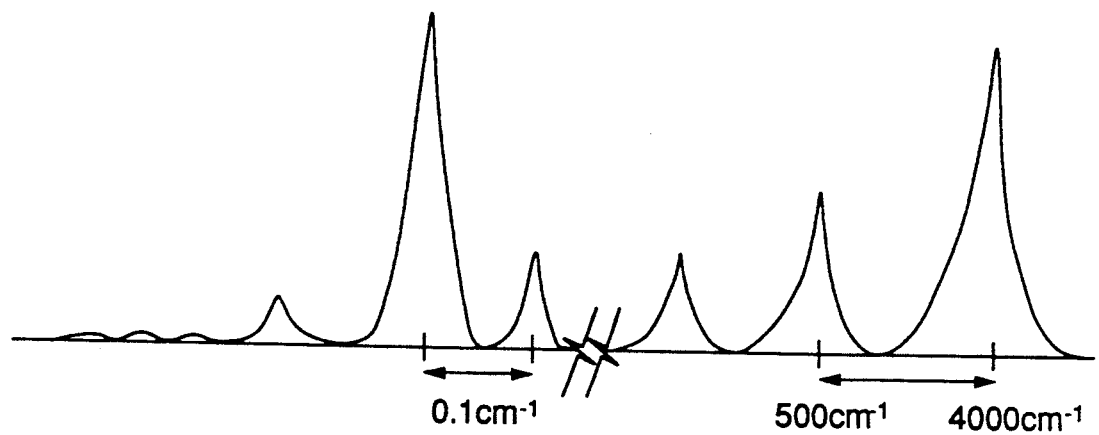
FIG. 2 illustrates a spectrum of frequency shifts that represent Raman scattering in response to the operation of the invention.

FIG. 2 illustrates the spectral region in which the analysis is performed and which provides vibrational bands associated with the molecules comprising the sample. The range of frequency shifts illustrated in FIG. 2 may be obtained by either varying the wavelengths detected with monochrometer or by Fourier transform methods with an interferometer. Once the spectrum is obtained, the analysis of the Raman scattering is performed in the same manner as with other spectroscopic methods.

As indicated in FIG. 2, the frequency shifts are centered around the frequency of the incident radiation at 0 on the abscissa. The frequency shifts of interest are in the range of $9398^{-1}$ to $5898^{-1}$ (Stokes) or $9398^{-1}$ to $12898$ cm$^{-1}$ (Anti-Stokes), both being within plus or minus $3500$ cm$^{-1}$ from the incident frequency. Thus, the frequency shifts are in the range of 0 to $4000$ cm$^{-1}$, which is the usual range of interest for Raman spectroscopy.

The spectral line centered at 0 frequency in FIG. 2 is referred to as the Rayleigh line. As indicated in FIG. 2, the intensity of this Rayleigh line is very much stronger than that of the Raman scattering. The Raman scattering lines shifted to the left of the Rayleigh line represent anti-Stokes scattering, and the lines shifted to the right represent Stokes scattering. At room temperature, the Stokes scattering is more intense, and is therefore usually the subject of analysis instead of the anti-Stokes lines. At higher temperatures, the intensity of the anti-Stokes and Stokes lines becomes more nearly equal. The temperature of the sample may be deduced from the intensity difference between the Stokes and anti-Stokes lines if the Boltzmann relationship is applied to the intensity difference.

An advantage of the invention, as compared to Fourier transform methods is that certain undesired effects of the Rayleigh line are avoided. In Fourier transform methods, the Rayleigh line approximates a delta function, which transforms to a constant or to a broad Lorentzian. The result is a base line that rapidly slopes upwards at low frequency and thus tends to obliterate the low frequency shifts. Thus, the practical low frequency limit for Fourier transform techniques is in the area of $400$ cm$^{-1}$. However, as will be explained in further detail below, the invention permits analysis of the area from 0 to $400$ cm$^{-1}$.

Figure 3:
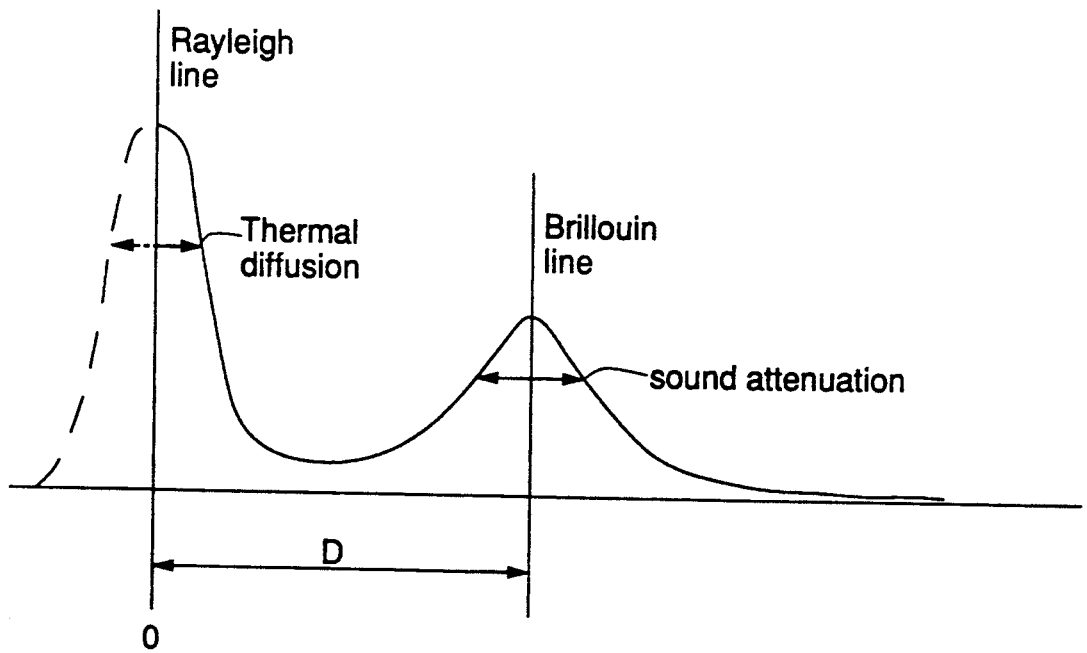
FIG. 3 illustrates the lower frequency shifts of FIG. 2.

FIG. 3 illustrates that part of FIG. 2 that is close to the zero frequency shift from the laser frequency. At these low wavenumbers, in the order of 1 cm$^{-1}$, the lines shifted to the immediate right and left of the Rayleigh line are known as the Brillouin scattering lines. In this part of the spectrum, the scattering can be thought of as a translational Raman scattering, as opposed to the rotational and vibrational scattering in the regions having greater frequency shifts. In the art of spectroscopy, the scattering in the region depicted in FIG. 3 is sometimes referred to as Rayleigh-Brillouin scattering.

All materials have vibrational responses in this low frequency region. Polymeric materials are especially good candidates for analysis with the present invention in the lower frequency shift region. For purposes of this description, this method of analysis is referred to as a "Brillouin scattering" method, as opposed to a "Raman scattering" method.

The width of the Rayleigh line at half height is directly proportional to the thermal diffusion coefficient. The width of the Brillouin peaks at half-height is directly proportional to a sound attenuation factor.

The ratio of the area of the central Rayleigh peak to that of the Brillouin peak is directly related to the ratio of the heat capacity at constant pressure to the heat capacity at constant volume, i.e., Cp/Cv. This ratio is known as the Landau Placzek ratio.

The distance, D, between the zero shift and the maximum height of the first Brillouin peak can be used analytically to obtain the sound characteristics of the sample:

$$D = C_s q$$

where Cs is the adiabatic sound velocity. The factor, q, may be expressed as follows:

$$q = \frac{4\pi n}{\lambda} \sin\Theta/2$$

, where λ is the wavelength of radiation source 11, n is the refractive index of the sample, and theta is the scattering angle. Referring again to FIG. 1, the determination of q is facilitated by configuring input fiber 12 and collection fibers 14 to equal a desired theta.

Analysis of the low frequency spectral lines in FIG. 3 may be performed with any type of frequency analyzer 16, if it provides sufficient resolution. In this regard, it is significant that the spectrum of FIG. 3 is approximately 6 gigahertz, which is between 0.1 and 0.2 $cm^{-1}$. For this reason, the preferred frequency analyzer 16 is a Fabry-Perot interferometer, which is a type of frequency analyzer 16 known in the art of spectroscopy.

In the simplest implementations of the invention, frequency analyzer 16 is a simple monochrometer, having a fixed grating adjusted to produce a single wavelength. Detector 17 is a diode array. The information of interest might be whether a spectral line is present at that wavelength, or, if a line is present, whether its intensity varies from that of a reference signature.

As an example of an application of the invention, it is especially useful during a cure process of a polymeric composite material. A known optimum cure cycle is used to obtain a reference Raman spectrum for the material to be analyzed. Sample temperatures may be quenched rapidly at different points in the cure cycle so as to produce reference spectra at various stages of cure. Peak positions and intensities are correlated with the degree of cure. Once the reference lines are obtained, unclad ends of input fiber 12 and collecting fibers 14 are imbedded in a sample of the material during the cure process. The analysis includes determining the properties of the sample, as well as void analysis. A probe head for this application is discussed below in connection with FIG. 4.

Figure 5:
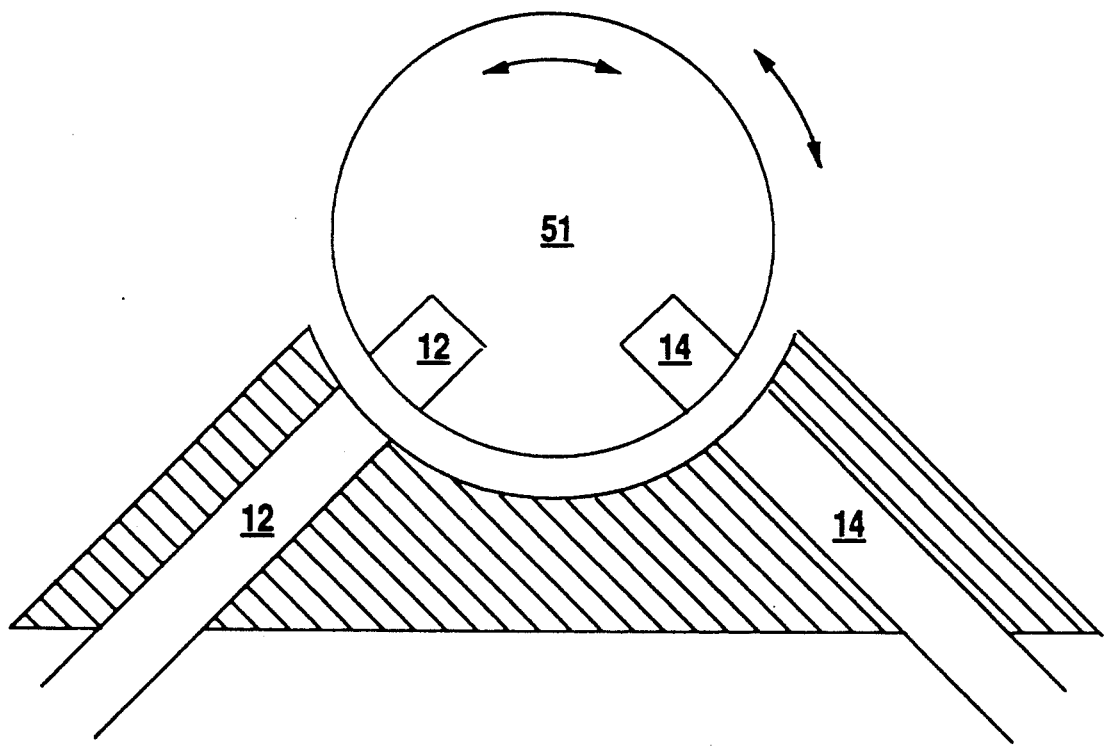
FIG. 5 illustrates a sensor for rotating parts.

In a second application of the invention, it is used with already cured polymeric materials. Again, the unclad ends are embedded in the material, but the analysis is directed to void formation, the void response to changes in applied pressure, or to the ingression of moisture or other fluids during the lifetime of the component. The use of fiber optics permits the invention to be used with rotating parts that would otherwise be inaccessible for real-time monitoring. A probe head for this application is discussed below in connection with FIG. 5. A stationary end of one fiber or fiber bundle could be placed in proximity to an end of another fiber or fiber bundle embedded in the rotating part 51, such that as the part 51 rotates, the two ends repeatedly establish communication with each other.

For example, the fiber could be embedded in a carbonfiber reinforced polymeric matrix laminated composite, which is part of a rotating part in an engine. As the stresses in the component change, these changes are reflected as changes in the position, i.e., frequency, and intensity of the low frequency Raman lines or Brillouin lines. These effects provide a means for in-situ sensing of internal stresses in laminated material or in the bondline of bonded structures. Because no mechanical or electrical contact is required, the measurement can be made while the component is rotating. Also, the fibers need only be a few microns in diameter, and are therefore suitable for hostile or otherwise physically inaccessible environments. Examples of such environments include the interior of high-temperature, high-pressure autoclaves used in the manufacture of composite materials or in the plastic body of a submarine or space station.

Figure 4:
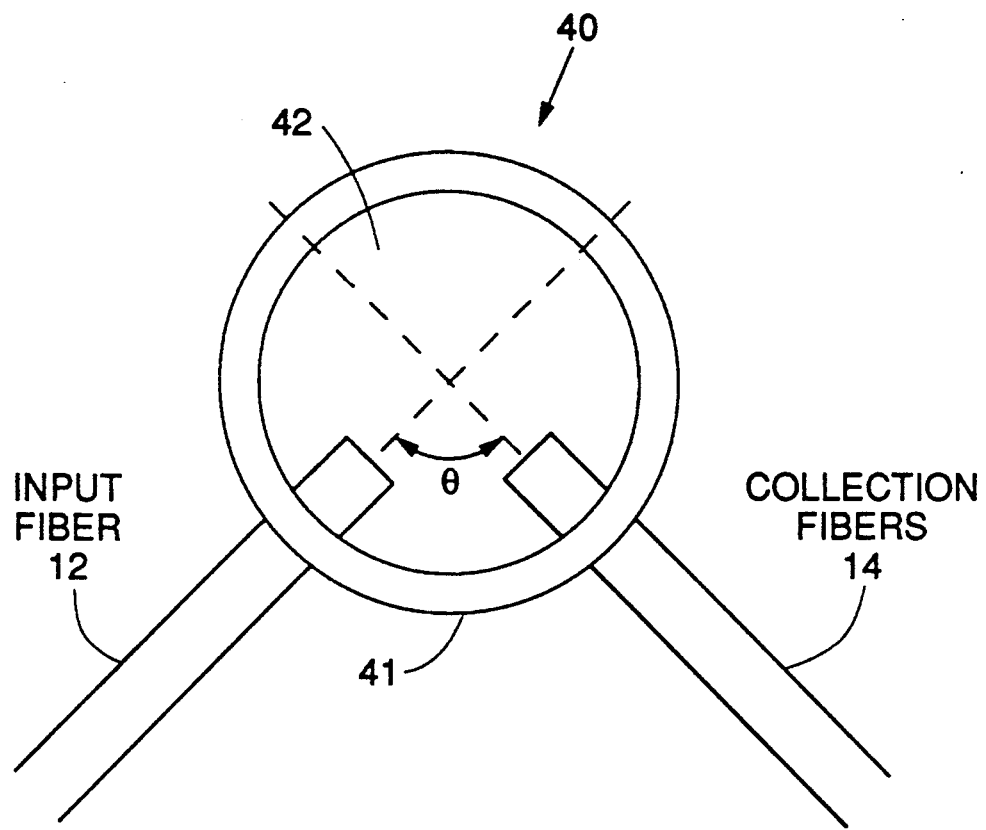
FIG. 4 illustrates a sensor for in-situ, real-time monitoring of materials.

FIG. 4 illustrates a probe head 40 that secures the unclad ends of input fiber 12 and collection fibers 14. A ring 41 holds these ends at a desired angle, Θ. Ring 41 is comprised of a suitable material such as a high temperature polyamide, having a cavity 42 for containing the sample. In operation, probe head 40 is simply placed into the material to be sampled.

OTHER EMBODIMENTS

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An apparatus for remotely performing a spectroscopic analysis of Brillouin and Raman scattered radiation from a sample of material, comprising:

a near-infrared laser for providing incident radiation, wherein the wavelength of said incident radiation is within a range of wavelengths between a fluorescence limit and a fiber optics loss limit, such that said incident radiation has a wavelength sufficiently long to minimize fluorescence from a material to be analyzed and sufficiently short to minimize optical fiber losses;

an input optical fiber for transmitting said incident radiation to a sample of material to be analyzed, wherein said input fiber is made from a low loss optical fiber;

at least one collecting optical fiber for receiving Brillouin and Raman scattered radiation from said sample, wherein said at least one collecting fiber is made from low loss optical fiber, wherein said input optical fiber and said at least one collecting optical fiber are placed at a predetermined angle with respect to each other;

an interferometer for receiving said scattered radiation from said at least one collecting fiber and for generating a fringe pattern representative of said scattered radiation over time;

a solid state infrared detector for detecting said fringe pattern and for producing a time-domain electrical signal representing intensities of said fringe pattern; and a processing means for transforming said time-domain electrical signal into a frequency-domain electrical signal representing intensities of said scattered radiation at different wavenumbers.

2. The apparatus of claim 1, wherein the wavelength emitted by said near-infrared laser is in the range of 1.0 micrometers to 2.0 micrometers.

3. The apparatus of claim 1, wherein said input optical fiber and said at least one collecting optical fiber are made from a heavy metal fluoride.

4. The apparatus of claim 1, wherein fibers are made from a fluoride material.

5. The apparatus of claim 1, wherein said angle is fixed by means of a probe head that secures the unclad ends of said optical fibers.

6. The apparatus of claim 1, wherein said interferometer is a Fabry-Perot interferometer.

7. The apparatus of claim 1, wherein said laser is a yttrium aluminum garnet laser.

8. The apparatus of claim 1, wherein said laser is a kryton ion laser.

9. A Brillouin and Raman scattering method of analyzing materials, comprising the steps of:

radiating a sample of the material to be analyzed, using near infrared radiation transmitted through a low loss fiber optic input tube;

placing a receiving end of a low loss fiber optic output tube at a fixed and predetermined angle to said fiber optic input tube;

collecting Brillouin and Raman scattered radiation scattered by said material in response to said radiating step, using said low loss fiber optic output tube;

using an interferometer to generate a fringe pattern of said scattered radiation as a function of time;

using a detector to generate a time-domain electrical signal representative of said fringe pattern; and transforming said time-domain electrical signal into a frequency-domain electrical signal representative of intensities of said scattered radiation at different wavenumbers.

10. The method of claim 8, wherein said transforming step is performed with a computer programmed to perform a Fourier transform of said time-domain electrical signal.

11. The method of claim 9, further comprising the step of determining the width of the Rayleigh line at half height.

12. The method of claim 9, further comprising the step of determining the width of a Brillouin peak at half height.

13. The method of claim 9, further comprising the step of comparing the area of the Rayleigh peak to the area of a Brillouin peak.

14. The method of claim 9, further comprising the step of determining the distance between the zero shift from the wavelength of the incident radiation to the wavenumber corresponding to the maximum value of Brillouin peak.

15. The method of claim 9, wherein said material is part of a rotating device, and further comprising the step of placing stationary ends of said optic fiber input tube and said fiber optic output tube in proximity to ends of corresponding nonstationary fibers such that as the device rotates, the ends communicate with each other.

16. The method of claim 9, and further comprising the step of determining the temperature of said material by obtaining a spectrum of the scattered wavelengths and comparing the intensity of anti-Stokes and Stokes lines on a spectrum obtained by said detector.

* * * * *